(12) United States Patent
Jenkins

(10) Patent No.: US 10,001,459 B2
(45) Date of Patent: Jun. 19, 2018

(54) SYSTEM AND METHOD FOR PHASED ARRAY EDGE CARD

(71) Applicant: General Electric Company, Schenectady, NY (US)

(72) Inventor: Thomas R Jenkins, Lewistown, PA (US)

( * ) Notice: Subject to any disclaimer, the term of this patent is extended or adjusted under 35 U.S.C. 154(b) by 574 days.

(21) Appl. No.: 14/634,239

(22) Filed: Feb. 27, 2015

(65) Prior Publication Data

US 2016/0266069 A1  Sep. 15, 2016

(51) Int. Cl.
| | |
|---|---|
| *B06B 1/06* | (2006.01) |
| *G01N 29/04* | (2006.01) |
| *G01N 29/24* | (2006.01) |
| *G01N 29/26* | (2006.01) |

(52) U.S. Cl.
CPC ......... *G01N 29/043* (2013.01); *B06B 1/0622* (2013.01); *G01N 29/2468* (2013.01); *G01N 29/262* (2013.01); *G01N 2291/044* (2013.01); *G01N 2291/106* (2013.01); *G01N 2291/2634* (2013.01)

(58) Field of Classification Search
CPC .............. H01L 41/047; H01L 41/0973; H01L 41/0815; B41J 2/161
USPC ........................................ 310/324, 328, 365
See application file for complete search history.

(56) References Cited

U.S. PATENT DOCUMENTS

| | | | |
|---|---|---|---|
| 5,820,549 A | 10/1998 | Marian, Jr. | |
| 6,043,590 A * | 3/2000 | Gilmore ................ | B06B 1/0607 310/334 |
| 7,557,489 B2 * | 7/2009 | Petersen ............... | B06B 1/0622 310/311 |
| 8,286,488 B2 | 10/2012 | Meyer et al. | |
| 8,287,290 B2 | 10/2012 | Cohen | |
| 2009/0043204 A1 | 2/2009 | Pelissier et al. | |

(Continued)

FOREIGN PATENT DOCUMENTS

| | | |
|---|---|---|
| EP | 1681019 A1 | 7/2006 |
| JP | 2011066921 A | 3/2011 |
| WO | 2006131875 A2 | 12/2006 |

OTHER PUBLICATIONS

PCT Search Report and Written Opinion issued in connection with corresponding PCT Application No. PCT/US16/17052 dated May 19, 2016.

(Continued)

*Primary Examiner* — Derek Rosenau
(74) *Attorney, Agent, or Firm* — Mintz Levin Cohn Ferris Glovsky and Popeo, P.C.

(57) ABSTRACT

A system includes an ultrasound measurement probe. The ultrasound measurement probe includes a lower portion. The lower portion includes a delay block, an array of ultrasound transducers coupled to the delay block, and a first circuit board. The first circuit board further includes a first plurality of pins coupled to the array of ultrasound transducers. The ultrasound measurement probe also includes an upper portion removably coupled to the lower portion. The upper portion includes a second circuit board. The second circuit board further includes a second plurality of pins configured to couple with the first plurality of pins when the upper portion is removably coupled to the lower portion.

20 Claims, 7 Drawing Sheets

(56) References Cited

U.S. PATENT DOCUMENTS

2011/0248603 A1* 10/2011 Tezuka ................. A61B 8/4405
310/314

OTHER PUBLICATIONS

Harfang Microtechniques Inc.,DAAH probes, http://www.poyeshyar.com/pdf/DAAH%20Probes.pdf, Jan. 2007, 2 pages.

* cited by examiner

SYSTEM AND METHOD FOR PHASED ARRAY EDGE CARD

BACKGROUND

The subject matter disclosed herein relates generally to ultrasound measurement probes, and more particularly to phased array ultrasound measurement probes.

Ultrasound measurement probes are used to inspect test objects in order identify and/or characterize defects, flaws, and other anomalies in the test object. Phased array ultrasound measurement probes are particularly useful in measuring the thickness of materials subject to corrosion or other wear. Use of ultrasound measurement probes generally causes wear on the probe itself until the probe is worn down, resulting in the entire probe being replaced. A probe may be replaced if a probe with a longer cable length is desired, such as when scanning a larger area. A probe may also be replaced if a different test controller is used, as test controller manufacturers may use probe connectors with different configurations.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes an ultrasound measurement probe. The ultrasound measurement probe includes a lower portion. The lower portion includes a delay block, an array of ultrasound transducers coupled to the delay block, and a first circuit board. The first circuit board further includes a first plurality of pins coupled to the array of ultrasound transducers. The ultrasound measurement probe also includes an upper portion removably coupled to the lower portion. The upper portion includes a second circuit board. The second circuit board further includes a second plurality of pins configured to couple with the first plurality of pins when the upper portion is removably coupled to the lower portion.

In a second embodiment, a method includes electrically connecting a first plurality of pins disposed on a first edge of a first circuit board of a first lower portion to a second plurality of pins of a second circuit board of a first upper portion. The first plurality of pins is configured to interface directly with the second plurality of pins. The method also includes removably coupling the first lower portion to the first upper portion to form a first ultrasound measurement probe. Each pin of the first plurality of pins is coupled to a first ultrasound transducer of a first array of ultrasound transducers of the first lower portion.

In a second embodiment, a method including an ultrasound measurement probe. The ultrasound measurement probe includes a lower portion. The lower portion includes a delay block and an array of ultrasound transducers coupled to the delay block. The array of ultrasound transducers includes a row of transmitter elements and a row of receiver elements. Each transmitter element is electrically connected to a first plurality of pins 1-32. Each receiver element is electrically connected to a second plurality of pins 1-32. The lower portion further includes a first housing disposed about the delay block and the array of ultrasound transducers. The first housing includes a plurality of indicators configured to indicate wear of the first housing a first circuit board. The first circuit board includes a third plurality of pins 1-80 at a first end portion of the first circuit board, where pins 1-8 and 73-80 are electrically connected to at least one grounding element; pins 9, 10, 13, 14, 17, 18, 21, 22, 25, 26, 29, 30, 33, 34, 37, 38, 41, 42, 45, 46, 49, 50, 53, 54, 57, 58, 61, 62, 65, 66, 69, and 70 are each electrically connected to a respective pin of the first plurality of pins 1-32; pins 11, 12, 15, 16, 19, 20, 23, 24, 27, 28, 31, 32, 35, 36, 39, 40, 43, 44, 47, 48, 51, 52, 55, 56, 59, 60, 63, 64, 67, 68, 71, and 72 are each electrically connected to a respective pin of the second plurality of pins 1-32; and the third plurality of pins is configured to electrically connect with a second circuit board of an upper portion of the ultrasound measurement probe at a second end portion of the first circuit board opposite the first end portion. The ultrasound measurement probe further includes an upper portion removably coupled to the lower portion. The upper portion includes a second circuit board, and the second circuit board comprises a fourth plurality of pins configured to couple with the third plurality of pins when the upper portion is removably coupled to the lower portion.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
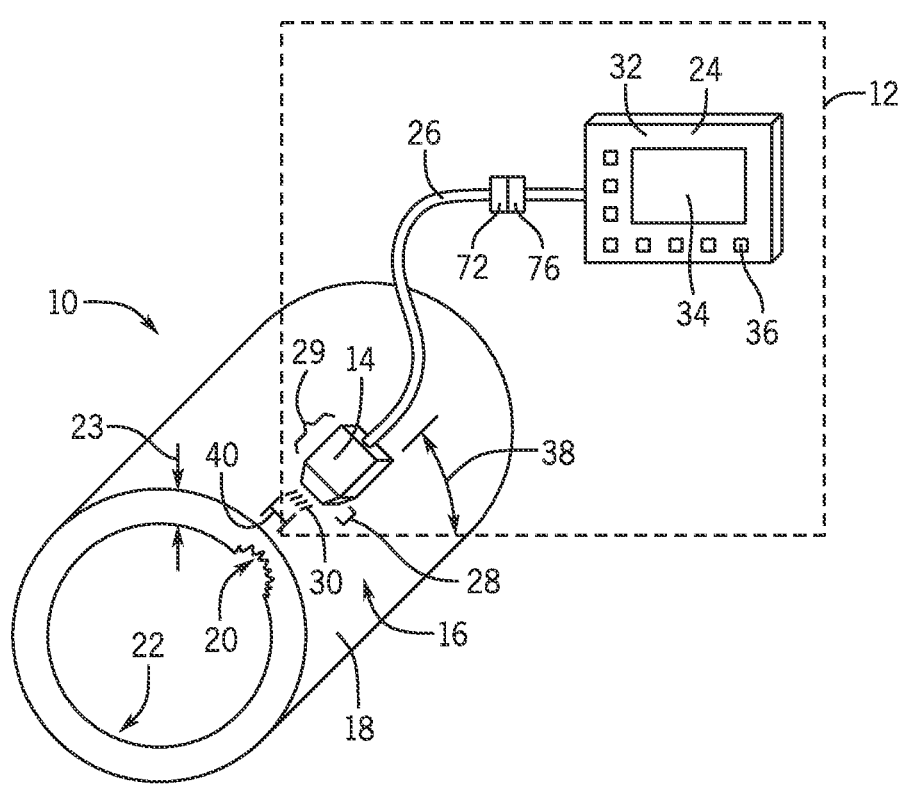
FIG. 1 is a perspective view of an embodiment of an application of a non-destructive measurement system having a non-destructive testing probe in accordance with the present disclosure.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions are made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The disclosed embodiments relate to multi-component or multi-section probes, which include a plurality of probe portions that removably couple together. These probes may include ultrasound probes, eddy current probes, visual inspection probes (e.g., borescopes), x-ray fluorescence (XRF) probes, non-destructive testing probes, or any combination thereof. The following discussion focuses on ultrasound measurement probes, but is intended to be inclusive of any probes including the examples provided above. The following discussion also focuses on handheld probes that are connected to a test controller, where the controls to direct and instruct the probe are located on the test controller and a user guides the probe with his hand. However, the following discussion is intended to be inclusive of any probes, including those that are not handheld or those that includes controls on the probe itself. Similarly, the disclosed embodiments refer to probe portions as upper and lower portions. However, it is appreciated that what is referred to as the lower portion is the portion of the probe that is in contact with, applied to, or otherwise directed toward the object to be tested. It is also appreciated that what is referred to as the upper portion is the portion of the probe that connects to the lower portion and couples to a cable that further couples to a test controller. References to features of the lower portion of the probe in the disclosed embodiments are not meant to necessarily limit those features to a portion of the probe that is closest to a relative "bottom." Likewise, references to features of the upper portion of the probe in the disclosed embodiments is not meant to necessarily limit those features to a portion of the probe that is closest to a relative "top." As mentioned above, referencing probe portions as upper and lower portions in the disclosed embodiments is not meant to limit the portions of the probe to two portions.

Ultrasound testing is a type of non-destructive testing that is used to inspect test objects in order to identify and/or characterize defects, flaws, and other anomalies in the test object. Testing equipment that is used in ultrasound testing generally includes an ultrasound measurement probe that sends and receives signals, a test controller that operates the probe, and a cable that transmits information between the probe and the test controller. In certain embodiments, the ultrasound measurement probe may be used to inspect pipe, machinery, or other industrial equipment. For example, the machinery may include compressors, pumps, and turbines, such as gas turbines, steam turbines, wind turbines, or hydro turbines.

The ultrasound measurement probe may incorporate transducer elements that are constructed of piezoelectric materials that are responsive to certain stimuli in a manner conducive to non-destructive testing. The transducer elements generate acoustic waves in response to electrical waveform pulses that are applied to electrodes connected to the transducer elements. These transducer elements are also responsive to acoustic waves, such as those acoustic waves that are reflected from the test object. For purposes of ultrasound testing, transducer elements are used to transmit acoustic waves into the test object and capture the reflection of those acoustic waves, where the resultant voltage differences across electrodes connected to the transducer elements caused by the reflected waves may be processed in order to analyze the test object.

Generally, ultrasound measurement probes are formed with at least transducer elements, electrodes, and circuitry elements disposed in a single, unitary body. For example, a potted sensor may utilize a filler material to form a unitary sensor structure that substantially encapsulates the transducer elements, electrodes, and circuitry elements of the ultrasound measurement probe. Use of ultrasound measurement probes generally causes wear on the probe itself, thereby limiting the usable life of the probe. A probe may be replaced if a probe with a longer cable length is desired, such as when scanning a larger area. A probe may also be replaced if a new test controller is used that has a different probe connector than was previously used.

The present disclosure provides an ultrasound measurement probe that includes a plurality of probe portions, (e.g., upper and lower portions) that are capable of being removably coupled together. The present disclosure also provides circuit boards disposed in each of the upper and lower portions whose pins are configured to be electrically connected together, such that the ultrasound measurement probe can then be operated when the upper and lower portions are removably coupled together. The lower portion is applied to the test object to inspect the test object. The lower portion includes a delay block or acoustic layer made of a delay material, an array of ultrasound transducers that is coupled to the delay material, and a first circuit board that includes a first plurality of pins that may be coupled to the array of ultrasound transducers at a first end of the first circuit board. The first plurality of pins may be disposed on an edge of the first circuit board at a second end of the first circuit board opposite the array of ultrasound transducers. The upper portion includes a second circuit board that includes a second plurality of pins that are configured to electrically connect to the first plurality of pins when the upper portion is removably coupled to the lower portion. The upper portion may include a cable assembly that couples to both the second plurality of pins and a cable that transmits information between the probe and the test controller. Advantageously, the ability to removably couple the upper portion with the lower portion, and thus electrically connect and disconnect the second plurality of pins from the first plurality pins, enables only the lower portion of the probe to be replaced when the probe is worn with use rather than the entire probe. Additionally, the modularity of the presently disclosed upper and lower portions of a probe enables the use of different cable lengths for different applications to be alternatively used with a single, removable, lower probe portion. Furthermore, the modularity of having removably coupled upper and lower portions of a probe allows different instrument connector options to be alternatively used with a single lower probe portion. Again, although the present discussion focuses on ultrasound measurement probes as an example, the disclosed embodiments are equally applicable to other types of probes (e.g., ultrasound probes, eddy current probes, visual inspection probes (e.g., borescopes), X-ray fluorescence (XRF) probes, non-destructive testing probes, or any combination thereof).

FIG. 1 is a perspective view of an embodiment of a system or application 10 of a non-destructive measurement system 12 (e.g., an ultrasound measurement system) having a non-destructive testing probe 14 (e.g., an ultrasound measurement probe 14) placed on a scan surface 16 of a test object 18. Again, as noted above, the system 12 and probe 14 may include any number of measurement techniques, such as ultrasound, eddy current, visual inspection, X-ray, or other non-destructive testing. Exemplary objects that can be interrogated by the ultrasound measurement system 12 as the test object 18 include, but are not limited to, pipes, ducts, plates, vessels, tanks, industrial equipment, compressors, pumps, turbines (e.g., wind, gas, hydro, and/or steam turbines), or any combination thereof. These test objects 18 may be susceptible to corrosion, thermal stress and cracking, mechanical stress and cracking, erosion, or other wear as shown by the recessed portion 20. For example, the recessed portion 20 may be a result of exposure to materials that cause oxidation of an opposing surface 22 that is opposite of the scan surface 16 of the test object 18.

In the present example, the ultrasound measurement probe 14 can have a lower portion 28 and an upper portion 29 that may be removably coupled. The lower portion 28 can have a scan area 30 that has a length 40. The length 40 of the scan area 30 can vary in a manner that permits the ultrasound measurement probe 14 to measure a variety of characteristics of the test object 18. These characteristics may include, but are not limited to, the material thickness 23 of the test object 18 and other defects, anomalies, and deviations (e.g., cracks, voids, and inclusions) 20 that may be located at different depths between the scan surface 16 and the opposing surface 22 of the test object 18.

The ability of the ultrasound measurement probe 14 to measure a variety of characteristics of the test object 18 is beneficial because the test object 18 can be interrogated in a manner that would normally utilize separate devices (e.g., devices optimized for detecting recessed portions 20 near the scan surface 16 of the test object 18 as opposed to deeper in the test object 18). It is likewise beneficial that the length 40 of the scan area 30 can be configured so as to substantially reduce both the interrogation time, as well as the likelihood that recessed portions 20 are missed during interrogation of the test object 18.

In the present embodiment of the ultrasound measurement system 12, a test controller 24 may be connected to the ultrasound measurement probe 14 by a cable 26 that exchanges information between the test controller 24 and the ultrasound measurement probe 14. The cable 26 may include a connector 72 to connect the probe 14 to a test controller 24 through the test controller connector 76 of the test controller 24. The test controller 24 may operate the probe 14 so as to activate, and collect data from, the scan area 30. Exemplary devices that are suited for use as the test controller 24 can include, but are not limited to, computers, ultrasound instruments, ultrasound systems, and the like. Examples of ultrasound instruments include the Phasor XS Ultrasonic Flaw Detector available from General Electric Inspection Technologies of Lewiston, Pa. and the OmniScan MX2 Phased Array Flaw Detector available from Olympus Corporation of Waltham, Mass.

By way of non-limiting example, the test controller 24 includes an interface 32 that has a display 34 that displays information, which can be collected by the ultrasound measurement probe 14. The interface 32 also includes one or more controls 36 (e.g., buttons, dials, switches, touch screen, etc.) that control the operation of the ultrasound measurement probe 14.

In view of the foregoing, and discussing one implementation of the ultrasound measurement probe 14 and the ultrasound measurement system 12 in application 10 in more detail, a user (e.g., a field engineer) can position the ultrasound measurement probe 14 on the scan surface 16 of the test object 18 so that the acoustic signals from transmitter elements 44 (FIG. 2) of the ultrasound measurement probe 14 enter the test object 18. The user can move the probe 14 along the scan surface 16 in a direction 38 that may be substantially perpendicular to the scan area 30. In the case of cylindrical test objects 18 (e.g., pipes), the direction 38 may be substantially circumferential and/or axial. Moving the probe 14 in this direction 38 may move scan area 30 over the area of interest of the test object 18. The term "area of interest" (or "AOI") is used herein to describe the portion of the test object 18 where data is to be collected with the ultrasound measurement system 12. An area of interest, for example, may include the test object 18 in its entirety, and/or a portion of the test object 18. The area of interest may also include portions of the test object 18 that are subject to corrosion, stress, or other wear as shown by the recessed portion 20. The area of interest may further include the scan surface 16 of the test object 18 in its entirety, and/or a portion of the scan surface 16 of the test object 18.

In one embodiment of the ultrasound measurement probe 14, the user can adjust the controls 36 of the test controller 24 so as to accommodate changes in the physical characteristics of the area of interest of the test object 18, including changes in the thickness 23 of the material between the scan surface 16 and the opposing surface 22 of the test object 18. For example, certain portions of the test object 18 may be subject to corrosion, stress, or other wear as shown by the recessed portion 20 such that the material thickness 23 of one portion of the test object 18 is different than the material thickness 23 of another portion of the test object 118. The physical characteristics also include the depth of the recessed portion 20 from the scan surface 16. For example, one recessed portion 20 may have a depth within the test object 18 that is different from other recessed portions 20 within the test object 18, which are also detected with the ultrasound measurement system 12. Additionally, or in the alternative, the physical characteristics may include a size or shape of the recessed portion 20.

Figure 2:
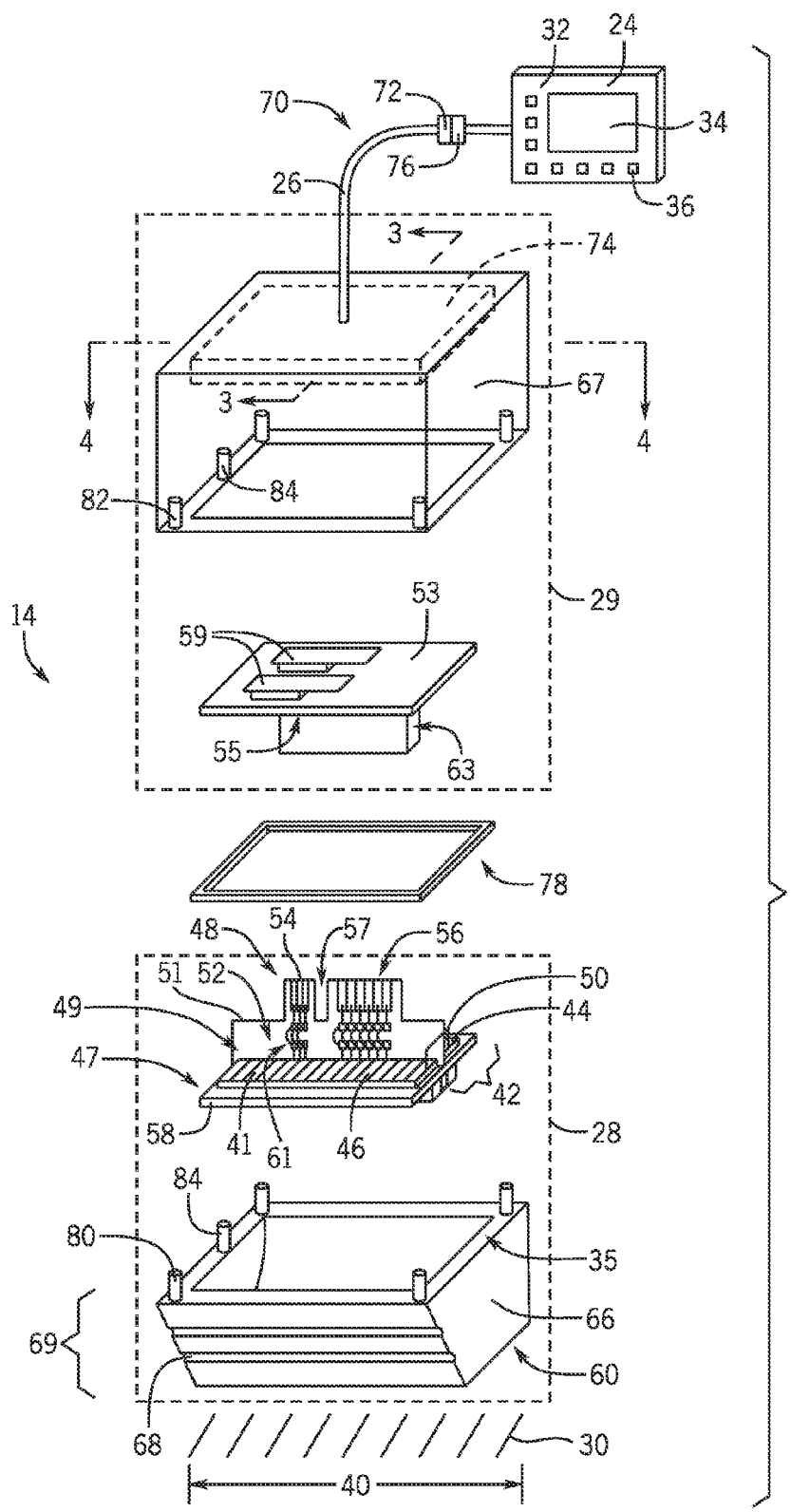
FIG. 2 is an exploded perspective view of an embodiment of a non-destructive testing probe in accordance with the present disclosure.
Figure 3:
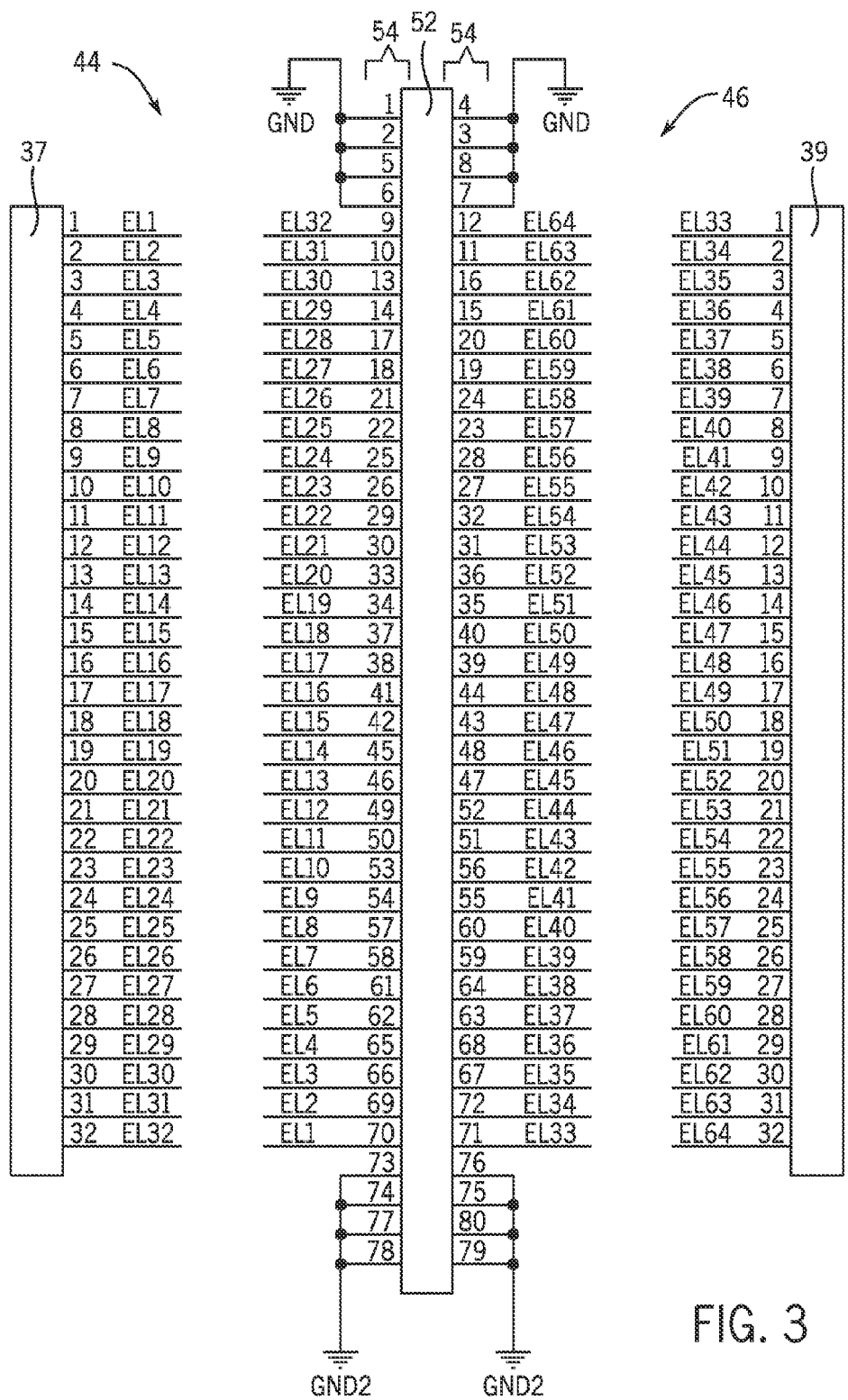
FIG. 3 is a schematic of electrical connections of an embodiment of a non-destructive testing probe in accordance with the present disclosure.

FIG. 2 is an exploded perspective view of an embodiment of a non-destructive testing probe (e.g., an ultrasound measurement probe 14) in accordance with the present disclosure. In the present example, the scan area 30 of the probe 14 includes a plurality of transducer elements (e.g., ultrasound transducer elements 41) arranged in an array 42. The array 42 of transducer elements 41 includes a plurality of transmitter elements 44 and a plurality of receiver elements 46. The plurality of transmitter elements 44 and receiver elements 46 may each be arranged in a row. For example, FIG. 3 is a schematic of electrical connections of an embodiment of a non-destructive testing probe in accordance with the present disclosure. FIG. 3 shows a mapping of pins for a row 37 of 32 transmitter elements 44 (labeled EL1-EL32) and a row 39 of 32 receiver elements 46 (labeled EL33-EL64). Each transmitter element 44 (labeled EL1-EL32) is mapped to a respective pin (labeled 1-32) of row 37. Each receiver element 46 (labeled EL33-EL64) is mapped to a respective pin (labeled 1-32) of row 39. The user may define how many transmitter elements 44 of row 37 and receiver elements 46 of row 39 will be active at any time during operation. There may be any number of transmitter elements 44 in row 37 and receiver elements 46 in row 39. For example, there may be 16 transmitter elements 44 in row 37 and 16 receiver elements 46 in row 39. As another example, there may be 64 transmitter elements 44 in row 37 and 64 receiver elements 46 in row 39.

The receiver elements 46 are configured to receive echo signals from the test object 18. Exemplary echo signals include, but are not limited to, acoustic signals and/or acoustic waves that correspond to the acoustic signals transmitted by the transmitter elements 44, and which are reflected back from the test object 18 toward the ultrasound measurement probe 14. Each of the transmitter elements 44 and the receiver elements 46 can be constructed, in whole or in part, of a piezoelectric material, including, for example, piezoelectric ceramics, lead zirconate titanate, lead matani-obate, piezoelectric crystals, and any combinations thereof. In one example, one or more of the transmitter elements 44 and one or more of the receiver elements 46 may include a 1-3 type piezocomposite material. In some embodiments, the transmitter elements 44 may be used as receiver elements 46, and vice versa.

The scan area 30 of the ultrasound measurement probe 14 may have one or more active groups 50. The active groups 50 may include a plurality of transducer elements 41, and more particularly the active groups 50 may include one or more of the transmitter elements 44 and one or more of the receiver elements 46. By way of a non-limiting example, each of the active groups 50 has at least one transmitter element 44 and transducer elements one receiver element 46, where the receiver element 46 receives the echo signals that correspond to the acoustic signals that originate from the transmitter element 44. In other examples of the ultrasound measurement probe 14, each of the active groups 50 includes any number of the transmitter elements 44 and the receiver elements 46. In one embodiment, active group 50 includes one to twenty transmitter elements 44 and one to twenty receiver elements 46. In another embodiment, active group 50 includes two to ten transmitter elements 44 and two to ten receiver elements 46. In another embodiment, active group 50 includes two to ten transmitter elements 44 and three to five receiver elements 46. The number of the transmitter elements 44 and the receiver elements 46 in the active groups 50 can be determined in accordance with the depth of the recessed portion 20 in the test Object 18. Greater quantities of transmitter elements 44 and receiver elements 46 enable detection of deeper recessed portions 20.

The test controller 24 that can be used in the present embodiment of the ultrasound measurement probe 14 can be configured to activate desired active groups 50 of the scan area 30. Additionally, or in the alternative, the test controller 24 can be configured to activate desired transmitter elements 44 and receiver elements 46. In some embodiments of the ultrasound measurement probe 14, the controls 36 of the test controller 24 can be configured to select the length 40 of the scan area 30, the number of active groups 50, and/or the number of the transmitter elements 44 and the receiver elements 46 in each of the active groups 50.

The lower portion 28 of the ultrasound measurement probe 14 includes a first circuit board 52 that has a first plurality of circuit board pins 54 (e.g., flat conductive contacts, pads, electrical contact points, etc.) coupled to the array 42 of ultrasound transducers elements 41 disposed at a first end 47 of the first circuit board 52. For example, FIG. 3 shows a mapping of circuit board pins 54 for the first circuit board 52 at the first end 47. Circuit board pins labeled 1-8 and 73-80 are connected to at least one ground or electrical common ground. Circuit board pins labeled 70, 69, 66, 65, 62, 61, 58, 57, 54, 53, 50, 49, 46, 45, 42, 41, 38, 37, 34, 33, 30, 29, 26, 25, 22, 21, 18, 17, 14, 13, 10, and 9 correspond to transmitter elements 44 (labeled EL1-EL32) of row 37 of array 42, which connect to pins labeled 1-32 of row 37 as described above. Pins 71, 72, 67, 68, 63, 64, 59, 60, 55, 56, 51, 52, 47, 48, 43, 44, 39, 40, 35, 36, 31, 32, 27, 28, 23, 24, 19, 20, 15, 16, 11, and 12 correspond to receiver elements 46 (labeled EL33-EL64) of row 39 of array 42, which connect to pins 1-32 of row 39 as described above. Because there may be any number of transmitter elements 44 in row 37 and receiver elements 46 in row 39, there may be a corresponding number of circuit board pins 54 of the first circuit board 52. For example, if there are 16 transmitter elements 44 in row 37 and 16 receiver elements 46 in row 39, there are at least 32 circuit board pins 54 for mapping to the transmitter elements 44 and receiver elements 46 of the first circuit board 52. As another example, if there are 64 transmitter elements 44 in row 37 and 64 receiver elements 46 in row 39, there are at least 128 circuit board pins 54 for mapping to the transmitter elements 44 and receiver elements 46 of the first circuit board 52. Additionally, while it is disclosed that the first plurality of circuit board pins 54 are expressly mapped as described above and illustrated in FIG. 3, it is appreciated that each of the first plurality of circuit board pins 54 may be mapped differently to other transmitter elements 44 (labeled EL1-EL32) and receiver elements 46 (labeled EL33-EL64). The first plurality of circuit board pins 54 may be coupled to the array 42 of ultrasound transducer elements 41 through the use of wiring harnesses 61. Embodiments of the probe 14 may include the first circuit board 52 oriented substantially perpendicular (between 85 and 95 degrees, or about 90 degrees) to the array 42 of ultrasound transducer elements 41. The first plurality of circuit board pins 54 may be disposed on an edge 56 of the first circuit board 52 at a second end 48 of the first circuit board 52 opposite the array 42 of ultrasound transducer elements 41. The first plurality of pins circuit board 54 may be disposed on one surface 49 of the first circuit board 52 and/or on the opposite surface 51 of the first circuit board 52. The first circuit board 52 may include a notch 57 to ensure that the first circuit board 52 is connected to the circuit board connector 63 of the upper portion 29 in a desired orientation.

The lower portion 28 of the ultrasound measurement probe 14 may also include a delay block 58 or acoustic layer that is coupled to the array 42 of ultrasound transducer elements 41 between the test object 18 and the array 42 of ultrasound transducer elements 41. The delay block 58 has a contact surface 60. The delay block 58 may acoustically couple, via the contact surface 60, the array 42 of ultrasound transducer elements 41 to the scan surface 16 of the test object 18. The delay block 58 may have a transmitter support surface 62 (FIG. 4) on which may be placed a plurality of transmitter elements 44. The delay block 58 may also have a receiver support surface 64 (FIG. 4) on which may be placed a plurality of receiver elements 46. The delay block 58 provides a barrier between the transducer elements 41 and the scan surface 16 of the test object 18 and adds a time delay to the time interval required for the wave to traverse the scan surface 16 of the test object 18 to be inspected. The delay block 58 is made of a delay material generally selected based on its acoustic velocity, or the velocity of the particles in the material as the material transmits an acoustic wave. The acoustic velocity of the materials in the delay block 58 may be different from the acoustic velocity of the materials of the test object 18. Exemplary delay materials for the delay block 58 include, but are not limited to, metals and plastics.

In some embodiments of the ultrasound measurement probe 14, the delay materials may include one or more of plastic, plexi-glass, and/or polystyrene.

The ultrasound measurement probe 14 includes a lower housing 66 for the lower portion 28 of the probe 14 that is disposed about the delay block 58 and the array 42 of ultrasound transducer elements 41. The lower housing 66 may have a wear portion 69 that includes indicators 68 (e.g., slots, notches, grooves, markings, or ridges) to show wear. For example, the wear portion 69 may have a number of horizontal indicators 68 spaced vertically along the lower housing 66. As the probe 14 is used, the part of the wear portion 69 that is in contact with the scan surface 16 of the test object 18 will wear. The space from the part of the wear portion 69 that is placed in contact with the scan surface 16 of the test object 18 to the closest indicator 68, along with the number of remaining indicators, indicate how much wear the wear portion 69 has undergone. The wear portion 69 of the lower housing 66 may be made of an abradable material, such that the hardness of the abradable material is less than that of the hardness of the material of the scan surface 16 of test object 18. Exemplary materials for use in the lower housing 66 include, but are not limited to, metals (e.g., aluminum, steel, brass, etc.), composites, and plastics, among many others.

The upper portion 29 of the ultrasound measurement probe 14 can include a second circuit board 53 that has a second plurality of pins 55 (e.g., flat conductive contacts, pads, electrical contact points, etc.) that may electrically connect to the first plurality of pins 54 located in the lower portion 28. The first plurality of pins 54 may be configured to interface directly with the second plurality of pins 55. For example, the first plurality of pins 54 and the second plurality of pins 55 may be configured such that they may be electrically connected using a male-female connector (e.g., first circuit board 52 of the lower portion 28 and a circuit board connector 63 and second circuit board 53 of the upper portion 29). It should be appreciated that the first circuit board 52 could alternatively have male and/or female connectors or pins and the second circuit board 53 could have corresponding female and/or male connectors or pins. The upper portion 29 includes an upper housing 67 disposed about the second circuit board 53. The upper portion 29 also includes a cable assembly 70 that couples to the second plurality of pins 55. The upper portion 29 of the probe 14 may include internal connectors 59 that couple the second circuit board 53 to the cable assembly 70. The cable assembly 70 includes a cable 26 that transmits information between the probe 14 and the test controller 24. One or more connectors 72 may also be disposed on the cable assembly 70. The one or more connectors 72 may couple the second circuit board 53 to a test controller connector 76 that corresponds to the test controller 24. As such, the test controller connector 76 of the test controller 24 may have a different configuration (e.g., pin layout) based on the make and/or model of test controller 24. For example, a Hypertronics model test controller connector 76, such as one available from General Electric Inspection Technologies of Lewiston, Pa., may have a different configuration 88 (FIGS. 4 and 5) than that of another Hypertronics test controller connector 76 or a test controller connector 76 manufactured by Omniscan (e.g., for the Omniscan MX2 Phased Array Flaw Detector) or Phasor (e.g., for the XS Ultrasonic Flaw Detector). In one embodiment of the probe 14, the one or more connectors 72 may couple the second circuit board 53 to a Hypertronics model test controller connector, an Omniscan model test controller connector, or a Phasor model test controller connector, or any combination thereof.

The upper portion 29 of the ultrasound measurement probe 14 may include a biasing element 74 coupled to the upper housing 67 and the second circuit board 53. The biasing element 74 urges the second circuit board 53 into contact with the first circuit board 52 of the lower portion 28 when the upper portion 29 is removably coupled to the lower portion 28. In some embodiments, the second plurality of pins 55 are biased pins configured to engage with the first plurality of pins 54. Non-limiting examples of a biasing element 74 include a spring or group of springs, a resilient material (e.g., rubber, foam, or plastic), or a combination thereof.

Figure 4:
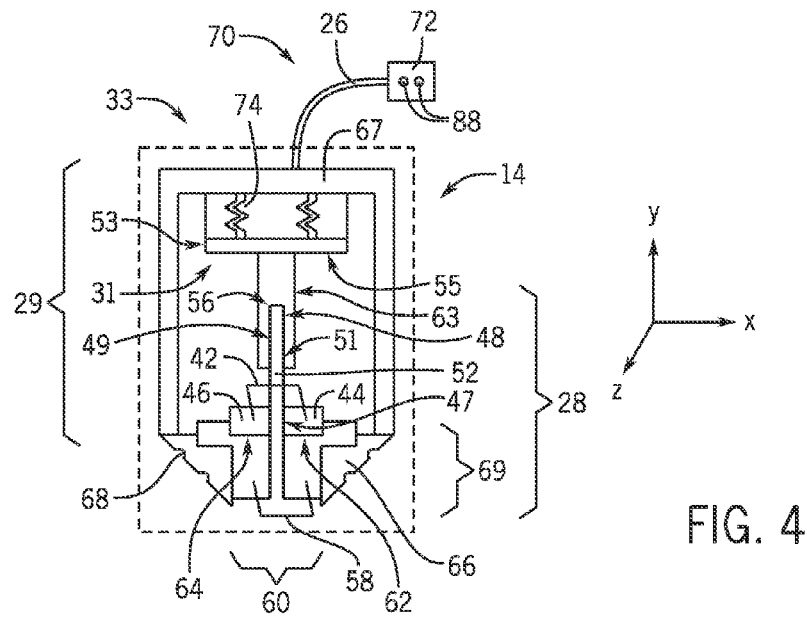
FIG. 4 is a cross-sectional side view of an embodiment of the assembled non-destructive testing probe of FIG. 2, taken along line 3-3.
Figure 5:
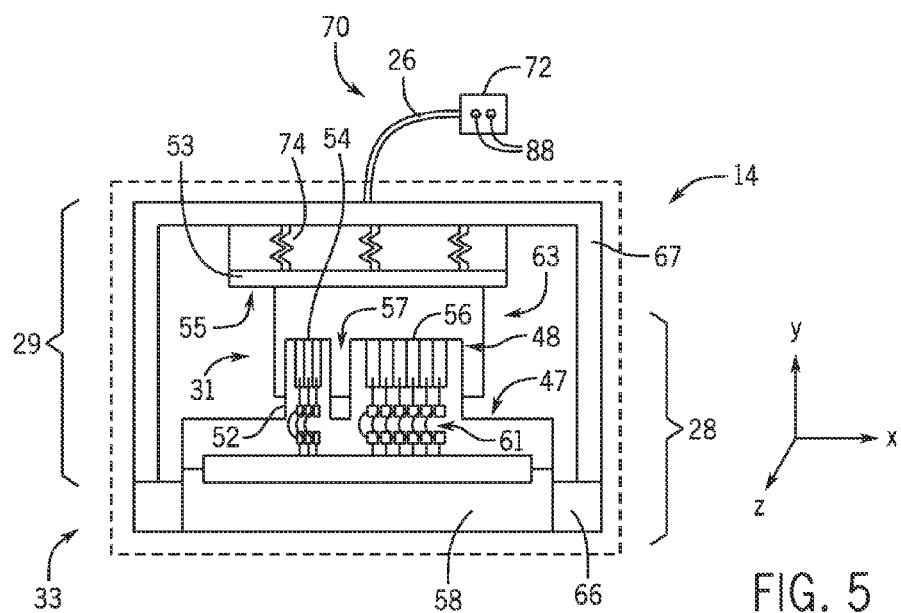
FIG. 5 is a cross-sectional side view of an embodiment of an assembled non-destructive testing probe of FIG. 2, taken along line 4-4.

The ultrasound measurement probe 14 may include at least one gasket 78 that can be disposed, for example, between the upper portion 29 and lower portion 28 of the ultrasound measurement probe 14 when the upper portion 29 and lower portion 28 are removably coupled. The lower portion 28 may include a sealing surface 35 that is configured to interface with the at least one of a gasket 78. The at least one gasket 78, with the upper portion 29 and lower portion 28, helps to seal the enclosure 31 and at least the first circuit board 52 of the lower portion 28 from the external environment 33 (FIGS. 4 and 5). The seal created by the at least one gasket 78 and upper portion 29 and lower portion 28 may be watertight, airtight, or a combination thereof. The gasket 78 may be made of an elastomer, a plastic, a fabric, or any combination thereof.

Removably coupling the lower portion 28 and the upper portion 29 may also include coupling the lower housing 66 to the upper housing 67. In some embodiments, first mating features 80 of the lower portion 28 and second mating features 82 of the upper portion 29 may be configured or disposed on the upper housing 67 and lower housing 66 such that the lower portion 28 and upper portion 29 can only interface in a desired orientation. For example, mating feature 84 (e.g., orientation guide) only allows the lower portion 28 and upper portion 29 of the probe 14 to be removably coupled in a desired orientation. The mating features 80 and 82 may include threaded fasteners (e.g., male and female threaded fasteners), snap-fit structures (e.g., male and female snap-fit structures), hooks and slots, latches, clamps, or any combination thereof.

FIG. 4 is a cross-sectional side view of an embodiment of the assembled non-destructive testing probe (e.g., the ultrasound measurement probe) of FIG. 2, taken along line 3-3. FIG. 5 is a cross-sectional side view of an embodiment of the assembled non-destructive testing probe (e.g., the ultrasound measurement probe) of FIG. 2, taken along line 4-4. Removably coupling the upper housing 67 to the lower housing 66 forms an enclosure 31 at least about the first circuit board 52 of the lower portion 28. The second plurality of pins 55 on the second circuit board 53 of the upper portion 29 are also electrically connected with the first plurality of pins 54 of the first circuit board 52 of the lower portion 28. The first circuit board 52 may be disposed such that it is substantially perpendicular (between 80 and 100 degrees) to the second circuit board 53 when the upper portion 29 is removably coupled to the lower portion 28. The first plurality of pins 54 may be disposed on the edge 56 of the first circuit board 53 and may be electrically connected with the second plurality of pins 55.

FIGS. 6-10 show different embodiments of non-destructive testing probes (e.g., ultrasound measurement probes 14) to illustrate how the upper portion 29 and lower portion 28 can be removably coupled and uncoupled to form different ultrasound measurement probes 14. As shown in the non-limiting example in FIG. 6, a first non-destructive testing probe (e.g., an ultrasound measurement probe 102) is formed by electrically connecting a first plurality of pins 54 of a first circuit board 52 of a first lower portion 28 with a second plurality of pins 55 on a second circuit board 53 of a first upper portion 29 and removably coupling the first lower portion 28 and the first upper portion 29. The first upper portion 29 may include a first cable assembly 70 that couples to the second plurality of pins 55. As discussed above, the first cable assembly 70 transmits information between the first ultrasound measurement probe 102 and a test controller 24. The first cable assembly 70 has a first cable 26 that has a first cable length 92 between the first upper housing 67 and the first connector 72. The first connector 72 may be used to couple the upper portion 29 of the first ultrasound measurement probe 102 to a test controller connector 76 that corresponds to the test controller 24. As illustrated, the first connecter 72 is of a first configuration 88.

Figure 6:
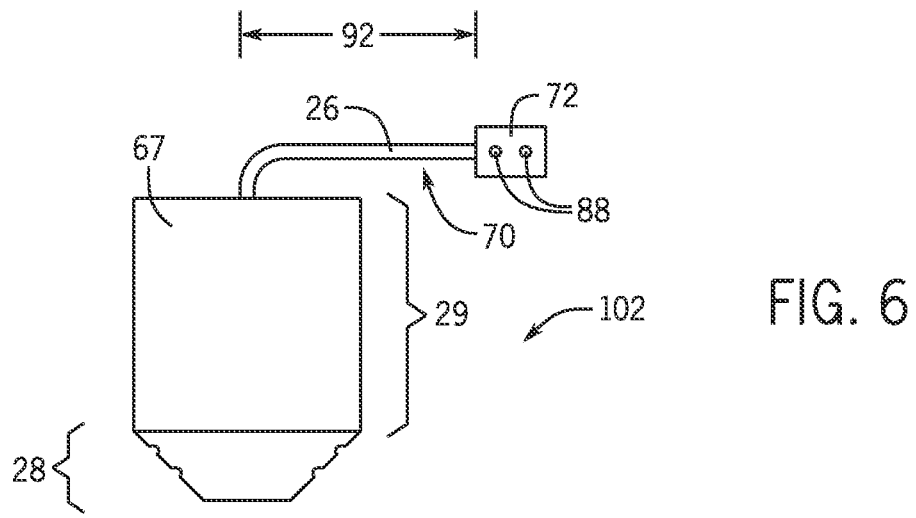
FIG. 6 is an embodiment of a non-destructive testing probe in accordance with the present disclosure.
Figure 7:
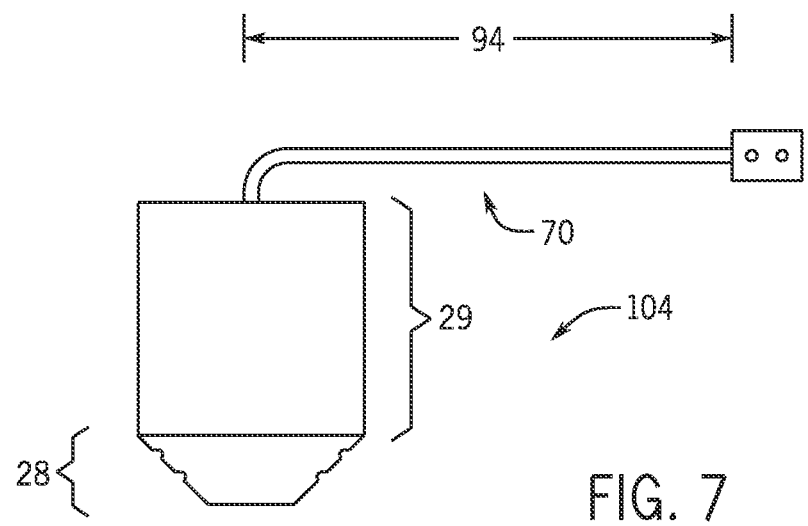
FIG. 7 is an embodiment of a non-destructive testing probe in accordance with the present disclosure.

As shown in the non-limiting example in FIG. 7, a second non-destructive testing probe (e.g., an ultrasound measurement probe 104) is formed by electrically connecting the first plurality of pins 54 with a third plurality of pins 55 on a third circuit board 53 of a second upper portion 29. In this example, a second cable assembly 70 of the second upper portion 29 includes a second cable 70 of a second cable length 94 that is different (e.g., greater) than the first cable length 92 as shown in FIG. 6. As may be appreciated, replacing the first upper portion 29 of the first ultrasound measurement probe 102 with the second upper portion 29 increases the overall range of the ultrasound measurement probe 104 due to a greater cable length 94 without replacing the entire probe 102.

Figure 8:
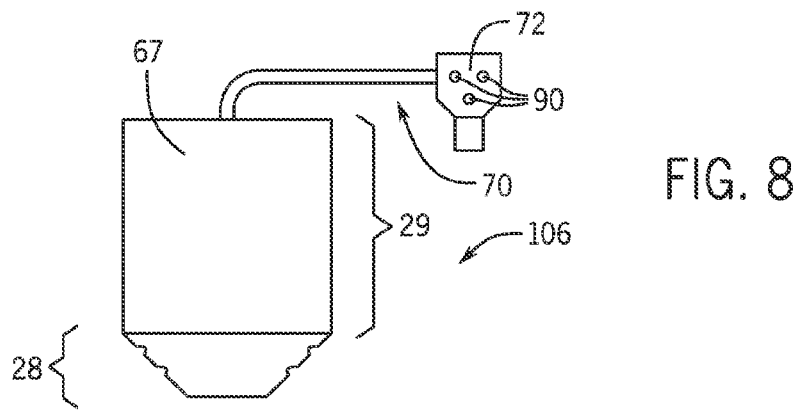
FIG. 8 is an embodiment of a non-destructive testing probe in accordance with the present disclosure.

As shown in the non-limiting example in FIG. 8, a third non-destructive testing probe (e.g., an ultrasound measurement probe 106) is formed by electrically connecting the first plurality of pins 54 with a fourth plurality of pins 55 on a fourth circuit board 53 of a third upper portion 29. In this example, a third cable assembly 70 of the third upper portion 29 includes a second connector 72 that has a second configuration 90 that is different than that of the first connector 72 that has a first configuration 88 as shown in FIG. 6. The third ultrasound measurement probe 106 may then be used with a test controller 24 that has a test controller connector 76 that can be mated with the second connector 72 with second configuration 90. As may be appreciated, replacing the first upper portion 29 of the first ultrasound measurement probe 102 with the second upper portion 29 enables the probe 106 to connect to a different test controller connecter 76, and thus a different test controller 24, without replacing the entire probe 102.

Figure 9:
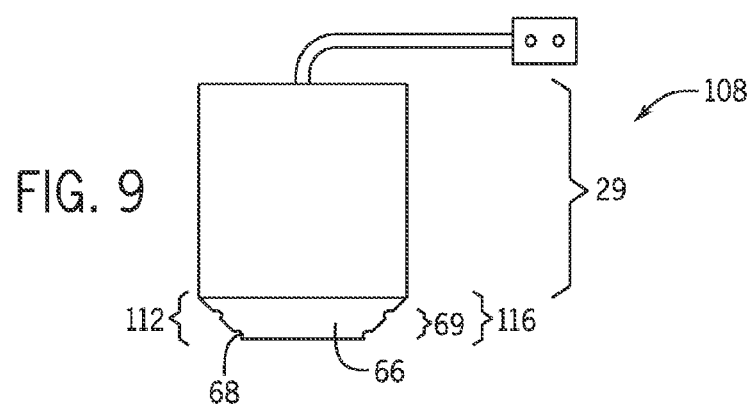
FIG. 9 is an embodiment of a non-destructive testing probe in accordance with the present disclosure.
Figure 10:
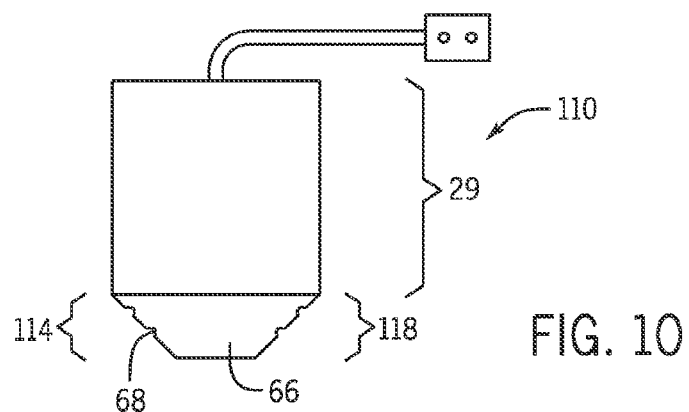
FIG. 10 is an embodiment of a non-destructive testing probe in accordance with the present disclosure.

FIG. 9 illustrates a fourth non-destructive testing probe (e.g., an ultrasound measurement probe) 108 formed by electrically connecting a fifth plurality of pins 54 of a fifth circuit board 52 of a worn second lower portion 112 with a sixth plurality of pins 55 on a sixth circuit board 53 of a fourth upper portion 29. In this example, the worn second lower portion 112 is worn from use, as can be seen by evaluating the indicators 68 on a wear portion 69 of a first lower housing 66, such that the first lower housing 66 is of a first thickness 116. The worn second lower portion 112 is replaced with a less worn (e.g., new) third lower portion 114 such that a fifth non-destructive testing probe (e.g., an ultrasound measurement probe 110) is formed, as shown in FIG. 10. As may be appreciated, the less worn third lower portion 114 has a second thickness 118 greater than that of the worn second lower portion 112 with a first thickness of 116.

Figure 11:
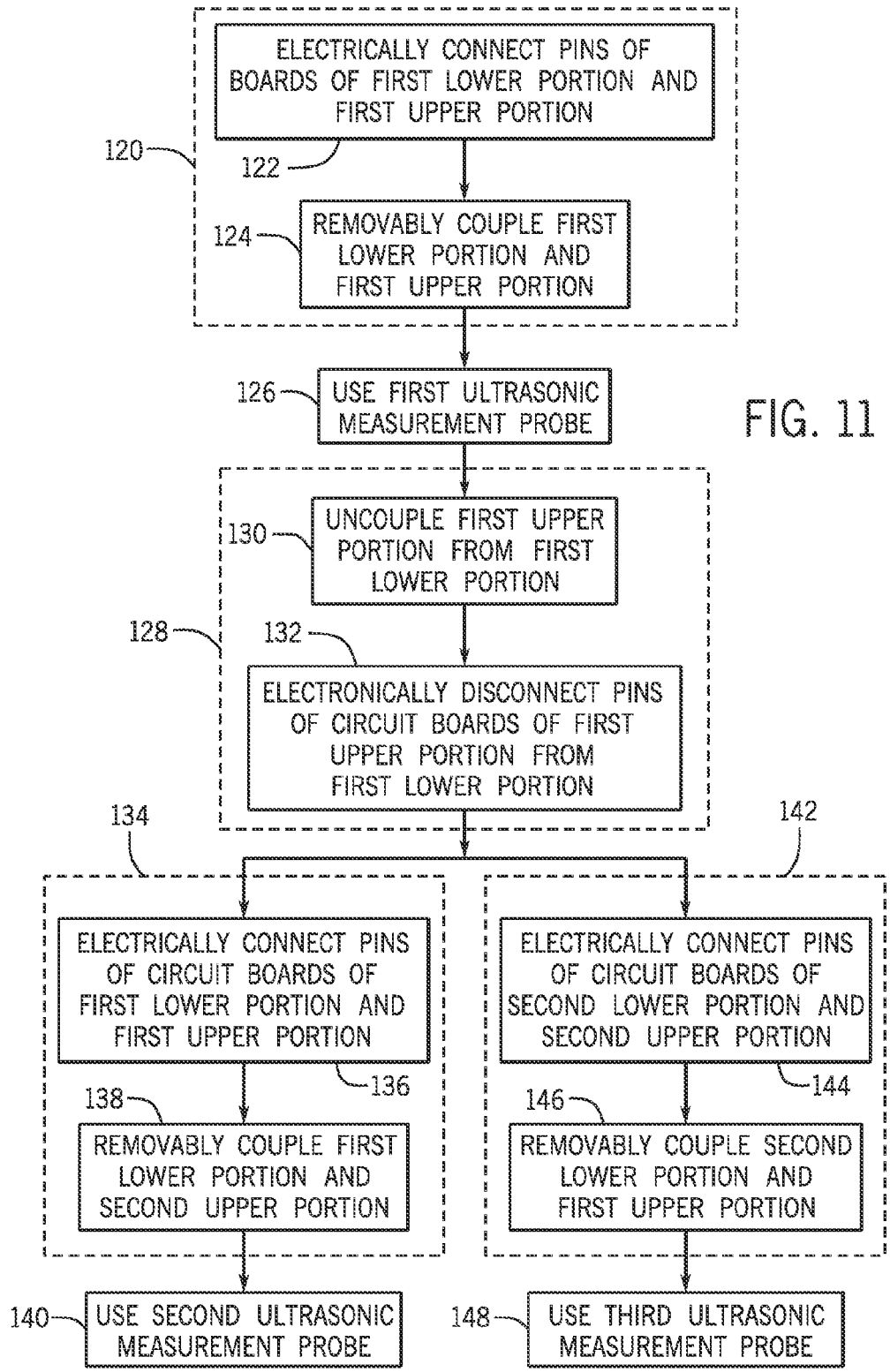
FIG. 11 is a flow chart illustrating the formation of an embodiment of a first non-destructive testing probe and subsequent formations of other probes from the upper and lower portions of the first probe.

FIG. 11 is a flow chart illustrating the formation of an embodiment of a first non-destructive testing probe (e.g., an ultrasound measurement probe 14) and subsequent formations of other embodiments of non-destructive testing probe (e.g., an ultrasound measurement probe 14) from the lower portion 28 and upper portion 29 of the first probe 14.

A first ultrasound measurement probe 14 is formed (block 120) by connecting a first plurality of pins 54 of a first circuit board 52 of a first lower portion 28 to a second plurality of pins 55 of a second circuit board 53 of a first upper portion 29 (block 122). Additionally, the first lower portion 28 and first upper portion 29 are removably coupled (block 124) when the first ultrasound measurement probe 14 is formed. The first ultrasound measurement probe 14 may then be used (block 126) to inspect test objects 18 in order identify and/or characterize defects, flaws, and other anomalies 20 in the test object 18.

The first ultrasound measurement probe 14 may be disassembled (block 128) to reduce and/or repurpose at least one of the first lower portion 28 and the first upper portion 29. First, the first upper portion 29 is uncoupled from the first lower portion 28 (block 130). Second, the first plurality of pins 54 is electrically disconnected from the second plurality of pins 55 (block 132).

In some embodiments, a second ultrasound measurement probe 14 may be formed (block 134) by electrically connecting the first plurality of pins 54 to a third plurality of pins 55 of a third circuit board 53 of a second upper portion 29 (block 136). Additionally, the first lower portion 28 and second upper portion 29 may be removably coupled (block 138) when the second ultrasound measurement probe 14 is formed. The first upper portion 29 includes a first cable assembly 70 coupled to the second circuit board 53 and the second upper portion 29 includes a second cable assembly 70 coupled to the third circuit board 53. As may be appreciated and as discussed in FIGS. 6-10 above, replacing the first upper portion 29 of the first ultrasound measurement probe 14 with the second upper portion 29 may increase the overall range of the probe 14 due to a greater cable length of the second upper portion 29 or enable the probe 14 to use other test controllers 24 without replacing the entire probe 14. The second ultrasound measurement probe 14 may then be used (block 140) to inspect test objects 18 in order identify and/or characterize defects, flaws, and other anomalies 20 in the test object 18.

In some embodiments, a third ultrasound measurement probe 14 may be formed (block 142) by electrically connecting a fourth plurality of pins 54 of a fourth circuit board 52 of a second lower portion 28 to the second plurality of pins 55 (block 144). Additionally, the second lower portion 28 and first upper portion 29 may be removably coupled (block 146). As may be appreciated, replacing the first lower portion 28 of the first ultrasound measurement probe 14 with the second lower portion 28 enables the user to replace the lower portion 28 of the probe 14 (e.g., due to wear of the lower portion's contact surface) extending the probe's lifetime without replacing the entire probe 14. The third ultrasound measurement probe 14 may then be used (block 148) to inspect test objects 18 in order identify and/or characterize defects, flaws, and other anomalies 20 in the test object 18.

Technical effects of the subject matter disclosed herein include, but are not limited to, forming an ultrasound measurement probe with upper and lower portions that can be removably coupled together. Disposing the pins of the circuit board of the lower portion on the edge of the circuit board of the lower portion facilitates this modularity by conveniently ensuring that the pins of the circuit board of the lower portion and the pins of the circuit board of the upper portion are securely connected when the portions are removably coupled. Advantageously, the ability to removably couple the upper portion from the lower portion and thus electrically connect and disconnect the pins of the circuit board located in the upper portion from the pins of the circuit board located in the lower portion enables only the lower portion of the probe to be replaced when the probe is worn with use rather than the entire probe. Additionally, a probe that is capable of removably coupling its upper and lower portions enables the use of different cable lengths for different applications to be used with a single, removable lower probe portion, thereby eliminating the need to acquire an entirely new probe with a desired cable length. Furthermore, the ability to removably couple a probe's upper and lower portions enables different instrument connector options to be used with a single, removable lower probe portion, thereby eliminating the need to acquire an entirely new probe with a desired instrument connector.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system comprising:
    an ultrasound measurement probe comprising:
        a lower portion comprising:
            a delay block;
            an array of ultrasound transducers coupled to the delay block; and
            a first circuit board comprising a first plurality of pins coupled to the array of ultrasound transducers;
        an upper portion removably coupled to the lower portion, wherein the upper portion comprises a second circuit board, and the second circuit board comprises a second plurality of pins configured to couple with the first plurality of pins when the upper portion is removably coupled to the lower portion.

2. The system of claim 1, wherein the lower portion comprises a first housing disposed about the delay block and the array of ultrasound transducers, the upper portion comprises a second housing disposed about the second circuit board, and the first housing and the second housing are configured to form an enclosure about the first circuit board when the second housing is removably coupled to the first housing.

3. The system of claim 2, comprising a gasket disposed between the first housing and the second housing when the upper portion is removably coupled to the lower portion.

4. The system of claim 2, wherein the upper portion comprises a biasing element coupled to the second housing and to the second circuit board, wherein the biasing element is configured to urge the second plurality of pins of the second circuit board into contact with first plurality of pins of the first circuit board when the second housing is removably coupled to the first housing.

5. The system of claim 1, wherein the first plurality of pins is disposed on an edge of the first circuit board opposite the array of ultrasound transducers.

6. The system of claim 1, wherein the first circuit board is substantially perpendicular to the second circuit board when the upper portion is removably coupled to the lower portion.

7. The system of claim 1, wherein the first plurality of pins are disposed on a first surface and an opposite second surface of the first circuit board.

8. The system of claim 1, wherein the upper portion comprises one or more connectors configured to electrically couple the second circuit board to a Hypertronics connector, an Omniscan connector, or a Phasor connector, or any combination thereof.

9. The system of claim 1, wherein the lower portion comprises first mating features and the upper portion comprises complementary second mating features, wherein the first mating features are configured to interface with the complementary second mating features in a desired orientation of the lower portion relative to the upper portion.

10. The system of claim 1,
    wherein the array of ultrasound transducers comprise:
        a row of transmitter elements, wherein each transmitter element is electrically connected to one of a third plurality of pins 1-32;
        a row of receiver elements, wherein each receiver element is electrically connected to one of a fourth plurality of pins 1-32; and
    wherein the first plurality of pins of the first circuit board comprise:
        pins 1-8 and 73-80 electrically connected to at least one grounding element;
        pins 9, 10, 13, 14, 17, 18, 21, 22, 25, 26, 29, 30, 33, 34, 37, 38, 41, 42, 45, 46, 49, 50, 53, 54, 57, 58, 61, 62, 65, 66, 69, and 70 each electrically connected to a respective pin of the third plurality of pins 1-32; and
        pins 11, 12, 15, 16, 19, 20, 23, 24, 27, 28, 31, 32, 35, 36, 39, 40, 43, 44, 47, 48, 51, 52, 55, 56, 59, 60, 63, 64, 67, 68, 71, and 72 each electrically connected to a respective pin of the fourth plurality of pins 1-32.

11. A method comprising:
    electrically connecting a first plurality of pins disposed on a first edge of a first circuit board of a first lower portion of a first ultrasound measurement probe to a second plurality of pins of a second circuit board of a first upper portion of the first ultrasound measurement probe, wherein the first plurality of pins is configured to interface directly with the second plurality of pins, wherein the first ultrasound measurement probe comprises a delay block; and
    removably coupling the first lower portion to the first upper portion to form the first ultrasound measurement probe, wherein each pin of the first plurality of pins is coupled to a first ultrasound transducer of a first array of ultrasound transducers of the first lower portion.

12. The method of claim 11, wherein removably coupling the first lower portion to the first upper portion comprises removably coupling a first lower housing of the first lower portion to a first upper housing of the first upper portion, wherein the first lower housing and the first upper housing are configured to form an enclosure about the first circuit board when the first upper housing is removably coupled to the first lower housing.

13. The method of claim 12, wherein removably coupling the first lower housing to the first upper housing comprises inserting a gasket between the first lower housing and the first upper housing, wherein the first lower housing, the gasket, and the first upper housing are configured to seal the enclosure and the first circuit board from an external environment.

14. The method of claim 12, comprising:
disassembling the first ultrasound measurement probe, comprising:
uncoupling the first upper portion from the first lower portion; and
electrically disconnecting the first plurality of pins from the second plurality of pins; and
assembling a second ultrasound measurement probe with the first lower portion, comprising:
electrically connecting the first plurality of pins of the first lower portion to a third plurality of pins of a third circuit board of a second upper portion, wherein the first plurality of pins is configured to interface directly with the third plurality of pins; and
removably coupling the first lower portion to the second upper portion to form the second ultrasound measurement probe.

15. The method of claim 14, wherein the first upper portion comprises a first connector coupled to the second circuit board, the second upper portion comprises a second connector coupled to the third circuit board, and the first connector is different from the second connector.

16. The method of claim 14, wherein the first upper portion comprises a first connector coupled to the second circuit board, the second upper portion comprises a second connector coupled to the third circuit board, the first connector comprises a first cable length, and the second connector comprises a second cable length different than the first cable length.

17. The method of claim 12,
disassembling the first ultrasound measurement probe, comprising:
uncoupling the first upper portion from the first lower portion; and
electrically disconnecting the first plurality of pins from the second plurality of pins; and
assembling a second ultrasound measurement probe with the first upper portion, comprising:
electrically connecting a third plurality of pins disposed on a second edge of a third circuit board of a second lower portion to the second plurality of pins of the first upper portion, wherein the third plurality of pins is configured to interface directly with the second plurality of pins; and
removably coupling the second lower portion to the first upper portion to form the second ultrasound measurement probe, wherein each pin of the third plurality of pins is coupled to a second ultrasound transducer of a second array of ultrasound transducers of the second lower portion, wherein the first lower portion comprises a first lower housing, the second lower portion comprises a second lower housing, and a first thickness of the first lower housing is less than a second thickness of the second lower housing.

18. The method of claim 11, wherein the second plurality of pins comprise biased pins configured to engage with the first plurality of pins on the first edge of the first circuit board, and the first circuit board is substantially perpendicular to the second circuit board when the first upper portion is removably coupled to the first lower portion.

19. The method of claim 11, wherein the first plurality of pins of the first circuit board comprise:
pins 1-8 and 73-80 electrically connected to at least one grounding element;
pins 9, 10, 13, 14, 17, 18, 21, 22, 25, 26, 29, 30, 33, 34, 37, 38, 41, 42, 45, 46, 49, 50, 53, 54, 57, 58, 61, 62, 65, 66, 69, and 70 each electrically connected to a transmitter element of the first array of ultrasound transducers; and
pins 11, 12, 15, 16, 19, 20, 23, 24, 27, 28, 31, 32, 35, 36, 39, 40, 43, 44, 47, 48, 51, 52, 55, 56, 59, 60, 63, 64, 67, 68, 71, and 72 each electrically connected to a receiver element of the first array of ultrasound transducers.

20. A system comprising:
an ultrasound measurement probe comprising:
a lower portion comprising:
a delay block,
an array of ultrasound transducers coupled to the delay block, comprising:
a row of transmitter elements, wherein each transmitter element is electrically connected to a first plurality of pins 1-32;
a row of receiver elements, wherein each receiver element is electrically connected to a second plurality of pins 1-32;
a first housing disposed about the delay block and the array of ultrasound transducers, wherein the first housing comprises a plurality of indicators configured to indicate wear of the first housing; and
a first circuit board comprising:
a third plurality of pins 1-80 at a first end portion of the first circuit board,
wherein pins 1-8 and 73-80 are electrically connected to at least one grounding element;
wherein pins 9, 10, 13, 14, 17, 18, 21, 22, 25, 26, 29, 30, 33, 34, 37, 38, 41, 42, 45, 46, 49, 50, 53, 54, 57, 58, 61, 62, 65, 66, 69, and 70 are each electrically connected to a respective pin of the first plurality of pins 1-32,
wherein pins 11, 12, 15, 16, 19, 20, 23, 24, 27, 28, 31, 32, 35, 36, 39, 40, 43, 44, 47, 48, 51, 52, 55, 56, 59, 60, 63, 64, 67, 68, 71, and 72 are each electrically connected to a respective pin of the second plurality of pins 1-32,
wherein the third plurality of pins is configured to electrically connect with a second circuit board of an upper portion of the ultrasound measurement probe at a second end portion of the first circuit board opposite the first end portion;
an upper portion removably coupled to the lower portion, wherein the upper portion comprises a second circuit board, and the second circuit board comprises a fourth plurality of pins configured to couple with the third plurality of pins when the upper portion is removably coupled to the lower portion.

* * * * *